United States Patent
Levinson (10) Patent No.: US 6,610,073 B1
(45) Date of Patent: Aug. 26, 2003

(54) SURGICAL CLIP, CLIP APPLICATOR AND METHOD THEREFOR

(75) Inventor: Melvin E. Levinson, Miami, FL (US)

(73) Assignee: Scion International, Inc., Miami, FL (US)

( * ) Notice: Subject to any disclaimer, the term of this patent is extended or adjusted under 35 U.S.C. 154(b) by 0 days.

(21) Appl. No.: 09/692,050

(22) Filed: Oct. 19, 2000

Related U.S. Application Data (60) Provisional application No. 60/160,387, filed on Oct. 19, 1999.

(51) Int. Cl.$^7$ ................................................. A61B 17/08
(52) U.S. Cl. ........................ 606/151; 606/153; 606/157
(58) Field of Search ................................ 606/151, 153, 606/157, 158, 213, 215, 216, 221, 116, 219, 75; 24/265 A, 295

(56) References Cited

U.S. PATENT DOCUMENTS

| | | | | |
|---|---|---|---|---|
| 3,068,870 A | * | 12/1962 | Levin | 606/221 |
| 3,326,216 A | | 6/1967 | Wood | 128/325 |
| 3,973,570 A | * | 8/1976 | Razgulov et al. | 606/153 |
| 4,188,953 A | | 2/1980 | Klieman et al. | 128/325 |
| 4,449,530 A | | 5/1984 | Bendel et al. | 128/325 |
| 4,539,990 A | * | 9/1985 | Stivala | 606/215 |
| 4,602,632 A | * | 7/1986 | Jorgensen | 606/158 |
| 4,971,198 A | | 11/1990 | Mericle | 206/339 |
| 4,972,949 A | | 11/1990 | Peiffer | 206/339 |
| 5,192,288 A | | 3/1993 | Thompson et al. | 606/143 |
| 5,217,473 A | * | 6/1993 | Yoon | 606/157 |
| 5,582,615 A | | 12/1996 | Foshee et al. | 606/139 |
| 5,709,706 A | | 1/1998 | Kienzle et al. | 606/205 |

OTHER PUBLICATIONS

Circon Product Brochure Snap–In/Snap–Out—Reposable Laparoscopic Instruments, Circon, Santa Barbara, CA. (p. 205)(circa 1999).
Circon Product Brochure Snap–In/Snap–Out—Laparoscopic Instrument Universal Handles, Circon, Santa Barbara, CA (p. 208)(circa 1999).

\* cited by examiner

*Primary Examiner*—Julian W. Woo
(74) *Attorney, Agent, or Firm*—Robert C. Kain, Jr.; Fleit, Kain (57) ABSTRACT

The surgical clip includes a U or a V shaped body having clip legs extending from its apex and terminal ends having a lateral span extending outboard from the clip. The terminal ends are shaped as triangles, ovals, a T, oblong or a wide end hexagonal shape. Sometimes, the terminal ends define outboard directed hooks. The clip's inboard surface may have gripping grooves. A clip applicator includes clip carrying jaws pivotally coupled and forming a mouth. Keyways capture clip ends. If the clip is hooked, the jaws define complementary latch openings. A system for closing the clip jaws may be linked scissor-like members, cam actuators and followers or cam follower surfaces. The clip applier may include tactile response indicators for the user to indicate partial or full jaw closure and full open-clip release positions.

13 Claims, 11 Drawing Sheets

SURGICAL CLIP, CLIP APPLICATOR AND METHOD THEREFOR

The present patent application is a regular patent application and claiming the benefit of provisional patent application Serial No. 60/160,387 filed Oct. 19, 1999.

The present invention relates to a surgical clip designed to be inserted into a small size access port on cannula, an associated clip applicator and a method therefor

BACKGROUND OF THE INVENTION

The current trend in minimally invasive surgery is to utilize smaller and smaller ports for access to the surgical site via cannulae or small tubes for insertion into body cavities. Currently, 5 mm ports are being utilized instead of the original 10 mm port for instrument access in laparoscopy and other types of minimally invasive surgery. In addition, 2 to 3 mm ports are being used for access and, as a result, smaller instruments are required to operate through these smaller ports and cannulae.

A frequently used instrument in minimal access surgery is a clip applier or clip applicator. This instrument is utilized in most operations for the ligation of vessels, tubular structures and other organs or organic bodies. One of the problem encountered by the reduction in size of the clip applier is that there is an irreducible dimension between the legs of the clip which is required to enable the clip to encircle the target structure (i.e.; blood vessel or other organic body). Since most clips are applied to the blood vessel or body in an open, incipient, clip-on position (excluding springs clips), the dimension exceeds 5 mm, precluding access through a 5 mm or smaller access port on cannulae. Clips small enough to be introduced through a small port (5 mm or less) lose their utility because the small opening between the jaws or the legs of the clip minimize the usefulness or utility of the clip.

The following patent disclosures show surgical clips: U.S. Pat. No. 3,326,216 to Wood; U.S. Pat. No. 4,188,953 to Klieman et al.; U.S. Pat. No. 4,449,530 to Bendel et al.; U.S. Pat. No. 4,844,066 to Stein; U.S. Pat. No. 4,971,198 to Mericle; U.S. Pat. No. 4,972,949 to Peiffer; U.S. Pat. No. 5,192,288 to Thompson et al.; U.S. Pat. No. 5,330,442 to Green et al.

The following patent disclosures show surgical instrument handles: U.S. Pat. No. 5,582,615 to Foshee et al. and U.S. Pat. No. 5,709,706 to Kienzle et al.

OBJECTS OF THE INVENTION

It is an object of the present invention to correct or circumvent the major problem of utilizing smaller and smaller access ports on cannulae by providing a specially designed surgical clip and an associated clip applicator.

It is another object of the present invention to provide a surgical clip which can be partially closed to reduce the clip leg span thereby permitting insertion into small access ports.

It is another object of the present invention wherein surgical clips, classified as medium, medium large, or large sizes (all currently requiring the use of larger than 5 mm access ports), can be inserted into 5 mm access ports (or smaller) when the clips are constructed in accordance with the principles of the present invention.

It is a further object of the present invention to provide surgical clips having terminal ends with a lateral span being larger than the span of the clip leg body such that the flare ends coact with channels on the clip jaws of the clip applicator thereby permitting the clip applier to partially close the captured clip prior to insertion through a small access port, then permitting expansion of the surgical clip after the clip and the clip jaws pass through the distal port on the cannula such that the clip can be opened to a full clip leg span and then applied, by compression, onto the blood vessel or other organic body.

It is a further object of the present invention to provide clip applier or clip applicator designs utilizing the specially designed surgical clips.

It is an additional object of the present invention to provide one tactile response to the operator indicative of a partially closed, insertion position or a fully closed position or a post deposition clip release position.

SUMMARY OF THE INVENTION

The surgical clip includes a U or a V shaped body having clip legs extending from its apex. The clip legs lie in an imaginary clip defined plane and the terminal ends of each clip leg have a lateral span extending outboard from the clip defined plane. The terminal ends, in certain embodiments, take the shape of a triangle, an oval, a T-shape, an oblong and a wide end hexagonal shape. In another embodiment, the clip's terminal ends include outboard directed hooks. The inboard surface of the surgical clip may have gripping grooves thereon. A clip applicator is utilized to carry the surgical clip to the surgical site. The clip applicator includes a first and a second clip carrying jaw pivotally coupled together to form a clip jaw mouth therebetween. At the distal end of each clip jaw, an open ended channel is formed as a keyway. The keyway is sized to capture a respective terminal clip end therein such that the terminal clip end acts as a key for the keyway when the clip is retained in the clip jaw mouth. If the clip defines hooked terminal ends, the clip jaws define complementary latch openings. The clip applier also includes a system for closing the clip jaws onto each other. The system for closing includes a variety of structures including linked scissor-like members, cam actuators and cam follower channels or cam follower surfaces responding to longitudinal movement of the cam actuators. In a preferred embodiment, the surgical instrument or clip applier includes tactile response indicators (which may be detents on the clip jaws or proximal jaw bodies) providing an indicator to the user that the clip jaws are in a partially closed, instrument insertion position or a fully closed clip compression position or a post deposition clip release position.

BRIEF DESCRIPTION OF THE DRAWINGS

Further objects and advantages of the present invention can be found in the detailed description of the preferred embodiments when taken in conjunction with the accompanying drawings in which:

FIGS. 3B and 3C diagrammatically illustrate a surgical clip with a hooked end wherein

DETAILED DESCRIPTION OF THE PREFERRED EMBODIMENTS

The present invention relates to a surgical clip, an associated clip applicator and a method therefor.

The present invention generally relates to a specially modified clip that has been designed for small access port insertion. The clip is constructed of the biocompatible material (titanium, stainless steel, etc.) and utilizes annealed or compressible metals or plastic materials. The distal tips of the legs of the clip are modified to a slightly expanded shape as compared to the remainder of the clip body so that a small portion of the terminal end of the legs of the clip are wider than the rest of the clip producing a slight "wedge" or "wing" configuration. This modification allows the clip to be held securely in a channel on the clip carrying jaws of the clip applier wherein the channel is slightly wider at the distal end. Utilizing this innovation, the clip can be picked up (individually or from a clip cartridge) compressed into the closed position, thereby minimizing its open clip profile and width of jaw distance, inserted through a small cannula, then opened to its incipient clip-on position and useful size by reopening the jaws of the applicator which pry the clip apart into its formerly open position.

It is in this configuration that the clip is applied to the structure (blood vessel or other organic body) and is then compressed again by the jaws of the clip applying instrument. Slight recoil of the clip applier jaws to a detent allows the applying instrument to slide off backwards from the closed clip. In order to facilitate this action, slack is provided between the expanded tip of the clip legs and its enclosing clip applier jaw channel so that no reopening of the clip occurs as the jaws recoil. The instrument is then slid backwards extricating the closed clip from the clip applier jaws and leaving it in the desired location and position.

The clip design utilizes clip shapes that can be compressed and then reopened to their previous shape and dimension. Such designs include a "U" shaped or a "V" shaped surgical clip. These designs serve this purpose well. Also, by providing appropriate detents in the clip applying instrument, partial closure only can be accomplished, thereby deforming the clip minimally to a partially open, clip insertion position prior to cannula insertion, final application and compression.

Closure sufficient to reduce the clip span and instrument to the internal diameter of the required port of the cannula is all that is necessary to achieve the required results.

The invention described herein provides a unique method for applying surgical clips of any reasonable size through extremely small access ports. This development is in keeping with the trend of utilizing smaller and smaller ports for minimally invasive surgery such as laproscopy, etc. Drawings provided herewith illustrate some applicable clip and instrument designs, but other designs are encompassed by the method of inserting the malleable clip and clip applier in a closed or partially closed position until the small dimensions of the access port are cleared. The clip is then opened by the jaws of the clip applicator, applied to the appropriate site and then compressed. This principle is incorporated into several clip and instrument designs for use in minimal access surgery.

Figure 1A:
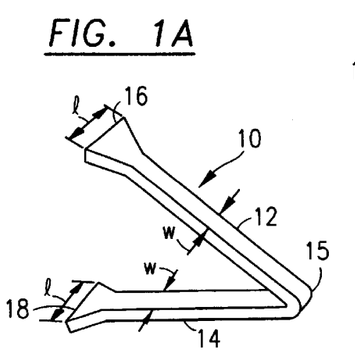
FIGS. 1A–1C diagrammatically illustrate surgical clips with flared terminal ends.

FIG. 1A diagrammatically illustrates surgical clip 10 having clip legs 12, 14 defining an apex 15 at one end thereof. Clip legs 12, 14 have a lateral width w which is substantially equal. Accordingly, the clip legs lie in an imaginary plane defined by the clip legs. The clip defined plane is normal or perpendicular to dimension w and both legs 12, 14 lie in the plane. Clip 10 includes terminal ends 16, 18 and these terminal ends have a lateral span 1 which extends outboard from the clip defined plane formed by legs 12, 14. In other words, terminal ends 16, 18 are wider (1) than the lateral span w of clip legs 12, 14. Clip 10 has a clip body defined by legs 12, 14 and apex 15. Similar numerals designate similar items throughout the drawings.

Figure 1B:
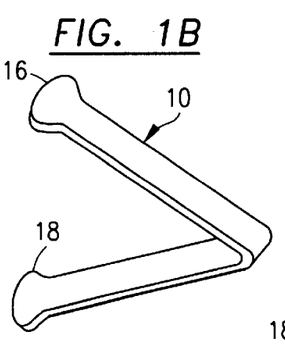

FIG. 1B diagrammatically illustrates surgical clip 10 wherein terminal ends 16, 18 have an oval or an oblong shape. In FIG. 1A, terminal ends 16, 18 have a generally triangular shape.

Figure 1C:
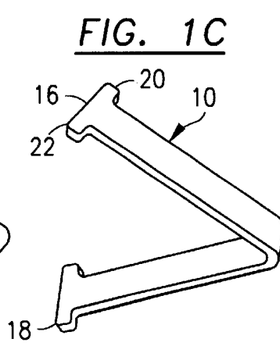

FIG. 1C diagrammatically illustrates surgical clip 10 wherein terminal ends 16, 18 have a T-shape. The horizontal portion of the T-shape is established by lateral wings identified as wings 20, 22 in connection with terminal end 16. FIGS. 1A–1C illustrate V-shaped surgical clip 10.

Figure 2:
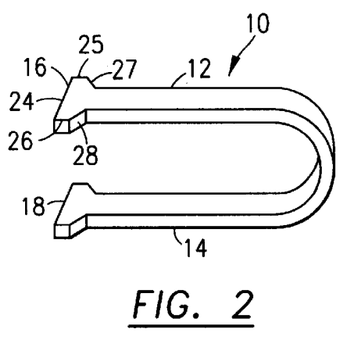
FIG. 2 diagrammatically illustrates a U-shaped clip in accordance with the principles of the present invention.

FIG. 2 shows a U-shaped surgical clip 10. Terminal ends 16, 18 define a wide end hexagonal shape. The wide end, hexagonal shape is established by terminal end surface 24, terminal side surfaces 25, 26, proximal angled surfaces 27, 28 and an imaginary rear end which is integral with clip leg 12. Preferably, surgical clip 10 is a one piece, integral body.

As used herein, the term "distal" refers to a feature of an item that is further removed from the surgeon or the user who operates the clip applier at a remote distance from the surgical site, that is, on a proximal end of the clip applicator or applier. As discussed later in connection with FIG. 7E, surgical clip 10 is compressed about a blood vessel or other organic body and terminal ends 16, 18 typically are remotely disposed at a distal end of the surgical instrument or clip applier.

As used herein, the term "substantially U or V-shaped body" refers to a clip which wraps upon itself such that the clip legs can be opened or closed. Further, the specific configuration of the terminal ends of the clip can take a variety of forms. One important feature with respect to the clip shown in FIGS. 1A–2 is that the terminal ends have lateral wings or laterally extending tabs, features or protrusions which act as keys fitted into keyways defined in the terminal end of clip jaws. The features are discussed later in connection with FIGS. 4, 5A, 5C and 6A–6E. The clips illustrated in FIGS. 1A–2 have flared terminal ends.

Figure 3A:
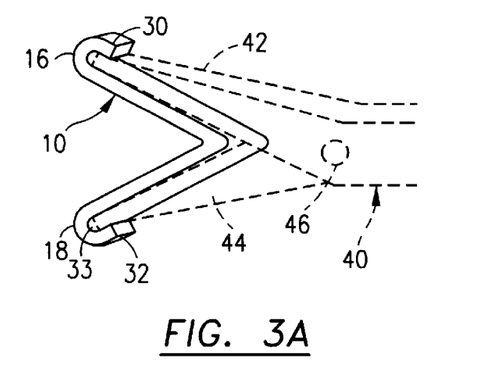
FIG. 3A diagrammatically illustrates a surgical clip wherein the terminal clip end includes an outboard hook and wherein the clip carrying jaws of the clip applicator are shown in broken lines.

FIG. 3A diagrammatically illustrates surgical clip 10 having hook ends 30, 32 at terminal ends 16, 18. Surgical instrument or clip applicator 40 is shown in broken lines. Clip applier 40 includes first and second clip jaws 42, 44 which, in the illustrated embodiment, pivot about common axis 46. Essentially, hook ends 30, 32 wrap around the terminal ends of clip jaws 42, 44.

Figure 3B:
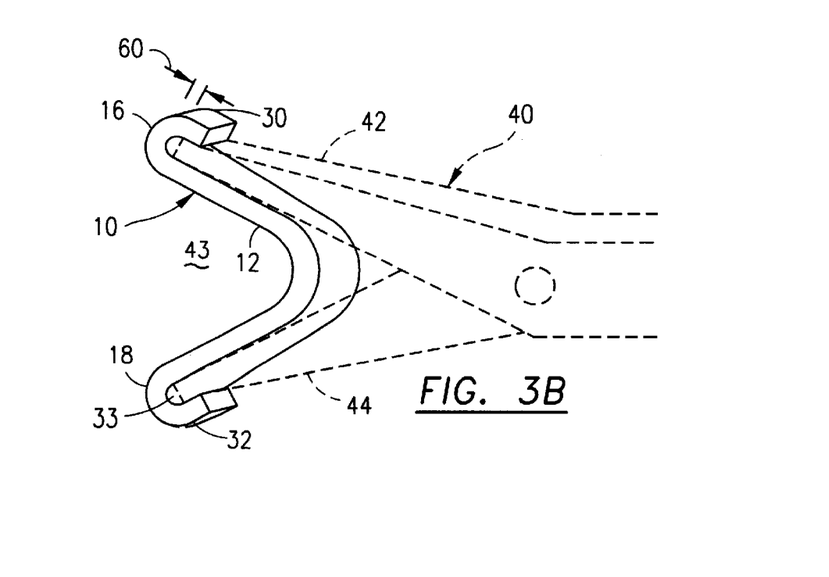
FIG. 3B shows a U-shaped clip and FIG. 3C diagrammatically illustrates a detail view of the clip applier wherein the surgical clip is shown in broken lines.

FIG. 3B diagrammatically illustrates a U-shaped surgical clip 10 with outboard hook ends 30, 32 retained at the distal end of clip applicator clip jaws 42, 44.

Figure 3C:
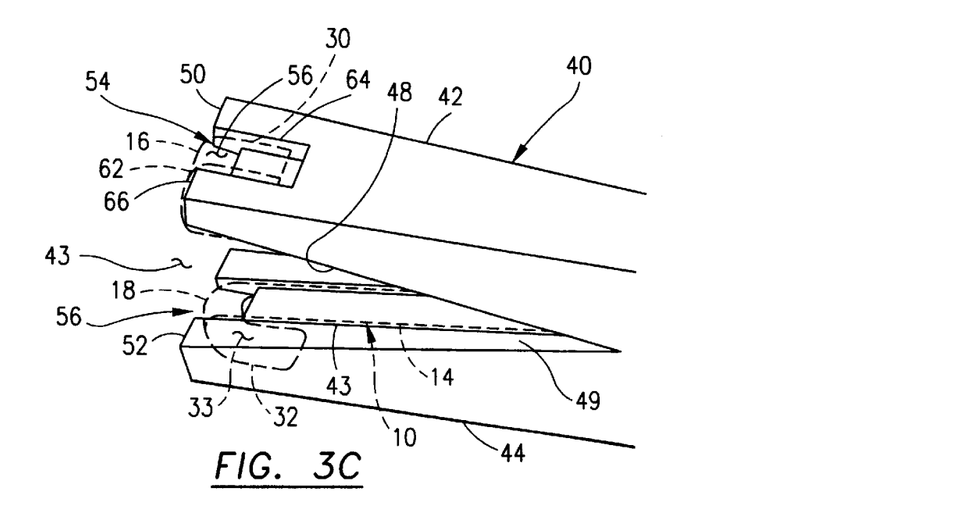

FIG. 3C diagrammatically illustrates clip jaws 42, 44 carrying clip 10 in clip jaw mouth 43. In the illustrated embodiment, surgical clip 10, shown in broken lines in FIG. 3C, has a clip leg 14 disposed in a shallow depth channel 43. Alternatively, inboard surfaces 48, 49 of clip jaws 42, 44, respectively, may provide an anvil surface without channel 43.

Clip jaws 42, 44 include distal ends 50, 52. Distal ends 50, 52 define latch openings 54, 56 which are generally complementary to outboard extending hooks 30, 32. In other words, hooks 30, 32 form hook mouths, one of which is hook mouth 33 shown in connection with hook 32. In the illustrated embodiment, latch opening 54 has a front end recess 56 generally equivalent to thickness or span 60 of hook 30 on clip leg 12 shown in FIG. 3B. In other words, terminal end surface 62 of hook end 30 shown in FIG. 3C is generally co-planar to terminal end surface 50 of clip jaw 42.

In FIG. 3B, the latch opening does not include sidearms. Sidearms 64, 66 are shown in FIG. 3C defining side walls of latch 54 and front end recess 56. Sidearms 64, 66 provide lateral stability to retain hook clip 10 on jaw 42. Further details of latch 54 are discussed later in connection with FIGS. 8A–8C.

Figure 4:
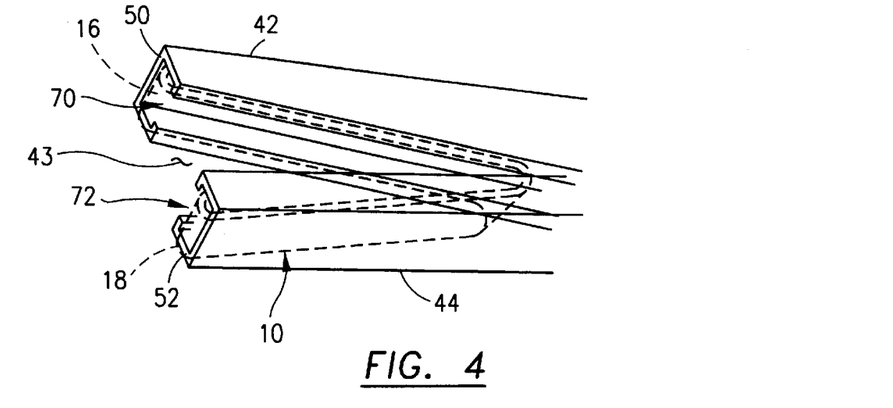
FIG. 4 diagrammatically illustrates a different construction for the clip applier wherein the surgical clip is shown in broken lines, FIGS. 5A, 5B and 5C diagrammatically illustrate various constructions of the open ended channel on the clip jaws (FIG. 5B shows the clip in the clip jaw mouth)

FIG. 4 diagrammatically illustrates clip 10 shown in broken lines and retained by clip jaws 42, 44. Clip jaws 42, 44 form a clip jaw mouth 43 therebetween. The distal ends 50, 52 of jaws 42, 44 are cut-away to form open ended channels 70, 72 which define keyways sized to capture terminal clip ends 16, 18 therein. Essentially, open ended channels 70, 72 form a respective keyway for a corresponding key configuration established by terminal clip ends 16, 18. As discussed later in connection with FIGS. 5A–5C and 6A–6E, the key and keyway created by terminal ends 16, 18 and open ended channels 70, 72 retain surgical clip 10 in clip jaw mouth 43. If the system is oriented with the longitudinal aspect of clip applier 40 on an imaginary x axis, side arms or side walls 64, 66 are displaced along the y axis and the hook ends 30, 32 extend in the z axis. As explained below, the clip 10 is loosely retained in the z axis. To adequately retain the clip in clip jaw mouth 43, the clip may be closely retained in the x and y axis.

Figure 5A:
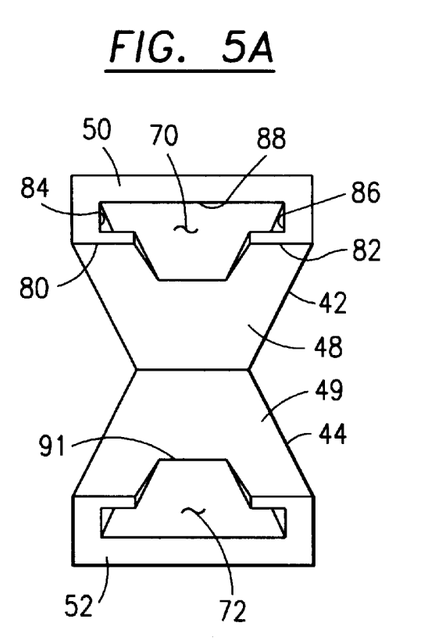
Figure 5B:
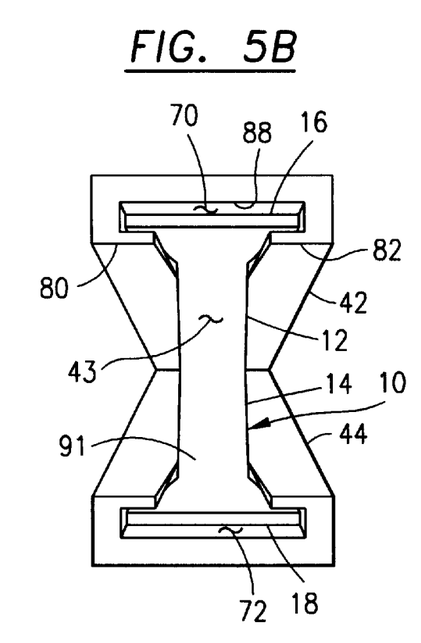

FIGS. 5A and 5B diagrammatically illustrate open ended channels 70, 72 defined on distal end surfaces 50, 52 of clip jaws 42, 44. FIG. 5B shows surgical clip 10 loosely retained in a z axis in open ended channels 70, 72. In the embodiment illustrated in FIG. 5A, channel 70 or keyway 70 is formed by roof elements 80, 82, sidewalls 84, 86 and a floor element 88. Floor element 88 slopes upwards until it reaches slope break line 89 separating the keyway or open ended channel 70 from anvil surface 48 of clip leg 42. Anvil surface 49 and slope break line 91, separating the floor from keyway 72, is shown in connection with lower clip jaw 44. Keyway or open ended channel 72 has a similar configuration as keyway 70.

In FIG. 5B, flared terminal clip ends 16, 18 are disposed in keyways 70, 72 thereby establishing flared ends 16, 18 as keys complementary in shape to keyways 70, 72. Roof elements 80, 82 enable the operator, by moving clip jaws 40, 42 in the z axis, to open clip 10 as necessary. Floor 88 forming keyway 70 and the corresponding floor for keyway 72 enable the operator, via clip jaws 42, 44, to close either partially or completely clip 10 disposed in clip jaw mouth 43. The anvil surface or proximal clip jaw portions are also utilized to close and compress the clip.

Figure 5C:
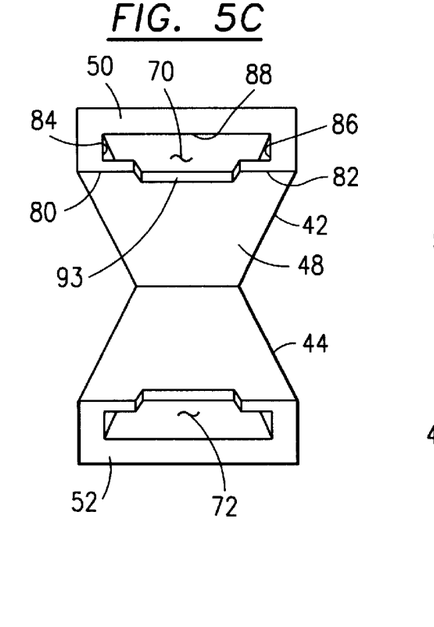

FIG. 5C shows a slightly different configuration for keyways 70, 72. Rather than a sloped surface established by floor 88, floor 88 is stepped or separated from anvil surface 48 by a step surface or step wall 93.

Figure 6A:
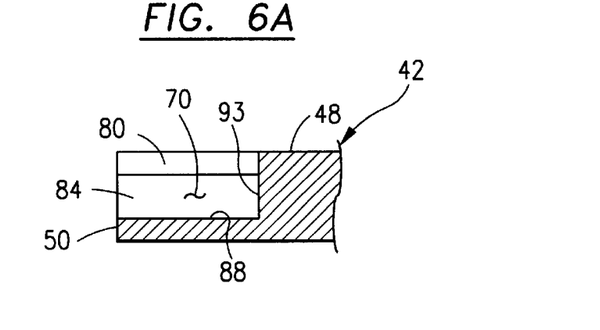
FIGS. 6A, 6B, 6C, 6D and 6E diagrammatically illustrate various aspects of the channel on the clip applier jaws.

FIG. 6A diagrammatically illustrates a detail, partial, cross-sectional view of the distal end of clip jaw 42. Keyway 70 includes roof element 80, floor 88, sidewall 84 and rear end sidewall or step 93. Sidewall step 93 is disposed proximally inboard with respect to distal end surface 50 of clip jaw 42.

Figure 6B:
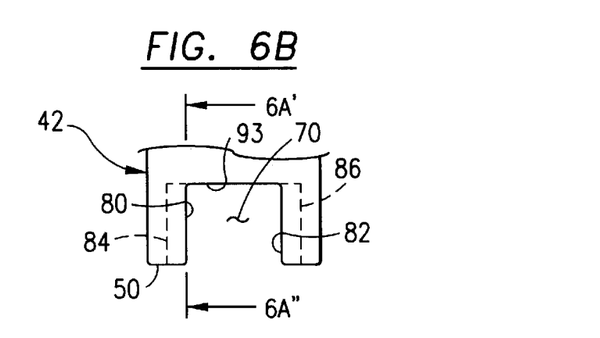

FIG. 6B shows a top, plane view of keyway 70 and shows that roof elements 80, 82 protrude laterally inboard into keyway 70 over sidewall surfaces 84, 86. FIG. 6A is a view from the perspective of section line 6A'–6A" in FIG. 6B.

Figure 6C:
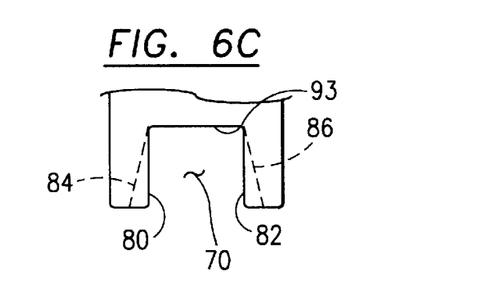

FIG. 6C shows a modification of keyway 70 wherein sidewalls 84, 86 are angled towards the longitudinal center line such that the open ended mouth of keyway 70 is laterally larger (y axis) than the proximal inboard portion of keyway 70 adjacent sidewall step 93. It should be noted that sidewall step 93 in FIG. 6C may be replaced by the slope break line 89 which separates keyway 70 in FIG. 5A from anvil surface 48 of clip leg 42.

Figure 6D:
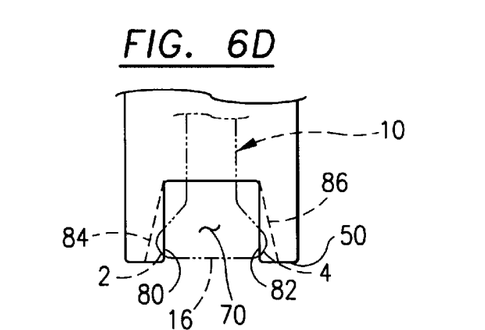

FIG. 6D shows flared terminal clip end 16, shown as a broken line, disposed in keyway 70. The lateral extensions 2, 4 of terminal end 16 are captured beneath roof segments 80, 82 of keyway 70.

Figure 6E:
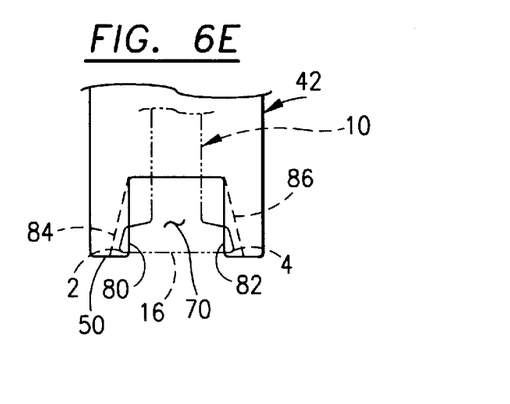

FIG. 6E shows that lateral tabs or extensions 2, 4 of flared terminal end 16 of clip 10 are closely captured and mate with sidewalls 84, 86 of keyway 70. This mating of side surfaces of the lateral flared tabs 2, 4 of terminal end 16 enable clip jaw 42 to capture clip 10 and position the clip at the terminal end surface 50 of clip jaw 42. FIG. 6D shows a loose fit (z axis) between flared end wings 2, 4 of clip end 16 as compared with sidewalls 84, 86.

Figure 7A:
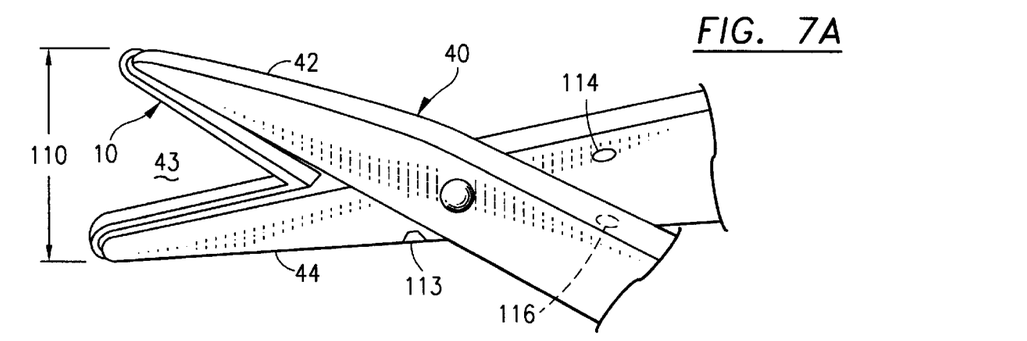
FIGS. 7A, 7B, 7D, 7E, 7F and 7G diagrammatically illustrate various operational positions of the clip carrying jaws and FIG. 7C diagrammatically illustrates one embodiment of the tactile response for the partially closed, instrument insertion position illustrated in FIG. 7B.
Figure 7B:
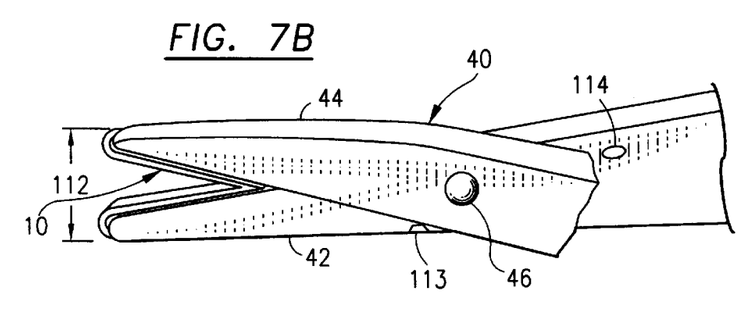
Figure 7C:
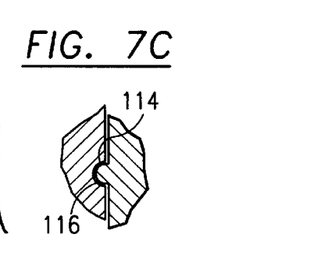

FIGS. 7A–7G generally show the operation of clip jaws 42, 44 and the clip action of clip 10 on a blood vessel or other organic body. FIG. 7C shows a tactile response mechanism configured as a detent providing a tactile response to the operator that the surgical clip is in a partially closed, instrument insertion position.

The following Closure Position Table (Operational Sequence) generally shows the sequential operation of the clip applier 40 in the present invention. The table immediately following entitled Closure Position Table (Mechanical Positions), lists the four (4) primary mechanical positions of the clip applier 40 ignoring the operational sequence shown in the earlier table.

Figure 7D:
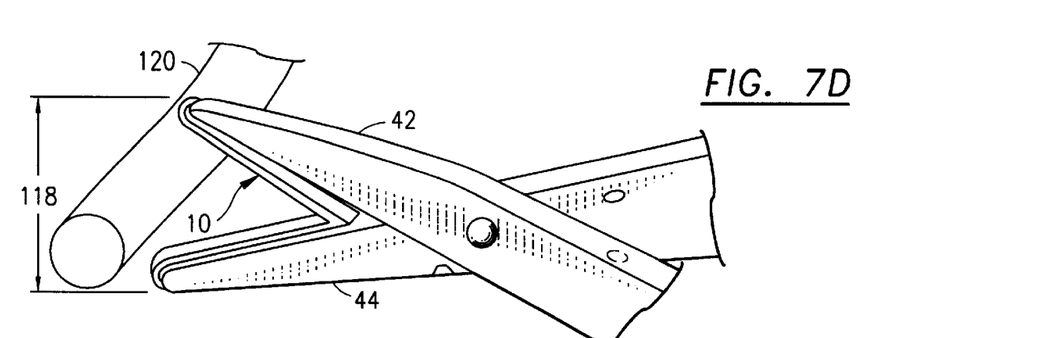
Figure 7E:
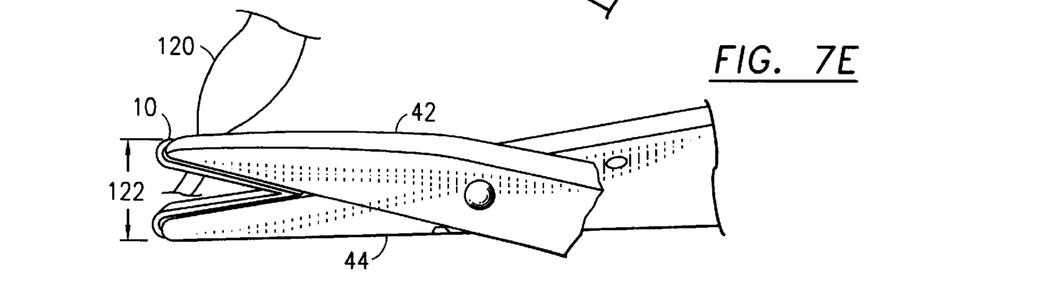
Figures 7F, 7G, 8A, 8B, 8C:
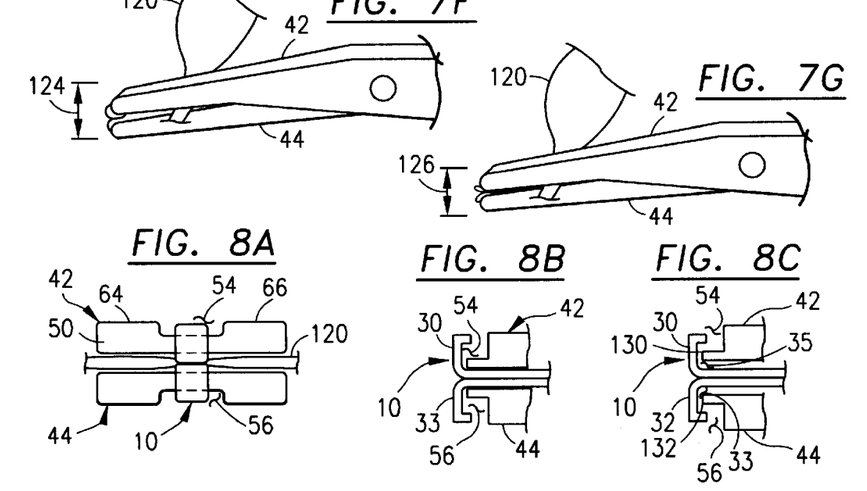
FIG. 8A and FIG. 9A diagrammatically illustrate a fully closed and compressed clip on a blood vessel or other organic body wherein the clip is a hooked end clip and a flare end clip, respectively (FIG. 7F diagrammatically illustrates the clip applier in the closed clip position)
FIG. 8B diagrammatically illustrates a side view of the hook end clip in the compressed clip or closed clip position.
FIGS. 8C, 9B and 9C diagrammatically illustrate the post deposition clip release position for the hook end clip (FIG. 8C) and the flare end clip (FIGS. 9B, 9C)

Closure Position Table (Operational Sequence)
  Full open (FIG. 7A)
  Partially closed for insertion (FIG. 7B)
  Full close for deposition on vessel or structure (FIG. 7F)
  Partial release for withdrawal of clip from jaw (FIG. 7G)

Closure Position Table (Mechanical Positions)
  Full open
  Partial close for insertion
  Partial clip release position
  Full close for clip deposition FIG. 7A diagrammatically shows clip applier 40 retaining surgical clip l0 in clip jaw mouth 43. Although surgical clip 10 is a hook end surgical clip is shown in FIG. 7A, a flared end surgical clip, similar to the one shown in FIGS. 1A–1C in FIG. 2, may be utilized. FIG. 7A diagrammatically illustrates clip jaws 42, 44 in a fully open position. In this full open position, clip jaw mouth 43 is open a distance 110. Clip 10 is disposed in clip jaw mouth 43 by an appropriate methodology discussed in connection with various clip holders. Persons of ordinary skill in the art understand this methodology.

In FIG. 7A, clip 10 is fully open since clip jaws 42, 44 are in their fully open position. In FIG. 7B, clip jaws 42, 44 are partially closed to a partially closed, instrument insertion position such that the span 112 of clip jaws 42, 44 (as well as the span of surgical clip 10) is small enough to enable insertion into a small access port and cannula for laproscopic or minimally invasive surgical procedures. Preferably, span distance 112 is smaller than 5 mm and possibly smaller than 2–3 mm. Clip jaws 42, 44 pivot about common axis 46. A small mechanical stop 113 in FIG. 7A limits the span 110 of clip jaws 42, 44. Returning to FIG. 7B, the operator is provided a tactile response by an indicator 114. As shown in FIG. 7A, indicator 114 on the proximal segment of jaw 44 cooperates with indicator 116 on the proximal segment of jaw 42. FIG. 7C shows that indicator 116 is a depression and indicator 114 is a protrusion or bump. In other words, tactile indicator response surfaces 116, 114 operate as detents in other to tactilely inform the user that surgical instrument or clip applier 40 is in the partially closed, instrument insertion position. After full insertion through the cannula and after clip jaws 42, 44 extend distally beyond the distal end or exit port of the cannula (not shown), clip jaws 42, 44 may be opened to span 118 (FIG. 7D) which is large enough to engage blood vessel 120 or other organic body element sought to be clipped by surgical clip 10. This is shown in FIG. 7D. Although a blood vessel 120 is shown in FIG. 7D, it should be understood by persons with ordinary skill in the art that other organic body structures may be clipped by surgical clip 10.

In FIG. 7E, clip jaws 42, 44 are partially closed thereby partially closing clip 10 about blood vessel 120.

FIG. 7F diagrammatically shows the fully closed or clip compressed position of clip jaws 42, 44. In this position, clip jaw span 124 is a minimal span distance.

FIG. 7G diagrammatically shows clip jaws 42, 44 slightly expanded such that clip jaw span 126 is larger than clip jaw span 124 shown in FIG. 7F. FIG. 7G shows clip jaws 42, 44 in a post deposition clip release position. This post deposition clip release position is discussed later in connection with FIGS. 8C and 9C.

FIGS. 8A–8C show the hook end surgical clip (see FIG. 3A) in the clip compression position (FIGS. 8A, 8B) and in the post deposition clip release position (FIG. 8C).

Figure 9A:
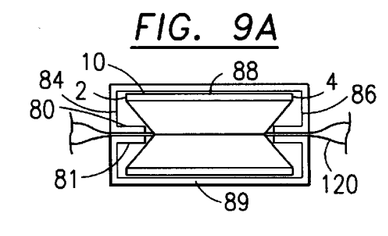
Figure 9B:
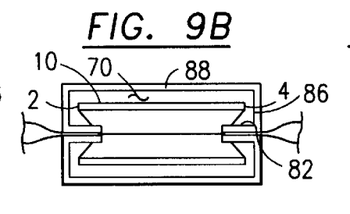
Figure 9C:
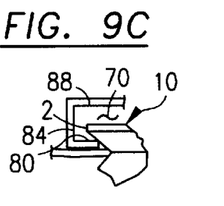

FIG. 9A shows a flared end clip in a keyway in a fully compressed position and FIGS. 9B and 9C show the jaws in the post deposition clip release position.

In FIGS. 8A–8C, the hook ends of clip 10 are disposed in latch openings 54, 56. As best shown in FIG. 8B, hook ends 30, 32 define hook mouths which are larger (on a z axis) than latch openings 54, 56. Hook mouths 35, 33 are shown in connection with hook ends 30, 32 in FIG. 8C. In FIGS. 8A and 8B, clip jaws 42, 44 flatten or compress clip 10 on blood vessel 120. Although blood vessel 120 is shown in these drawings, clip 10 could be placed on any other organic body structure. As shown in FIG. 8B, latch openings 54, 56 provide a space in the hook mouths defined by hook ends 30, 32. In FIG. 8C, clip jaws 42, 44 have been slightly opened to a post deposition clip release position such that the up turned extensions of hook ends 30, 32 (in the z axis) are essentially midway in latch mouths 54, 56. In other words, hook ends 30, 32, which establish hook mouths 35, 33, are larger in the z axis than the forward extensions 130, 132 defining latch openings 54, 56. In the post deposition clip release position, when the clip jaws are slightly opened a distance 126 shown in FIG. 7G, the latch openings 54, 56 enable the surgeon or user to proximally withdraw the clip jaws 42, 44 away from the clip 10 which has been deposited on blood vessel 120. Thereafter, the clip appliance 40 is placed in the partially closed for insertion position shown in FIG. 7B and the clip applier 40 is proximally withdrawn through the cannula by the surgeon or user.

FIGS. 9A–9C diagrammatically illustrate clip 10 in a compressed position (FIG. 9A) and in the post deposition clip release position (FIGS. 9B and 9C). FIG. 9A diagrammatically illustrates clip 10 having flare ends 2, 4 disposed in the keyway established by keyway floor 88, keyway sidewalls 84, 86 and keyway roof elements one of which is roof element 80. Clip 10 has been fully collapsed onto blood vessel 120. This position is similar to that shown in connection with FIG. 7F. FIGS. 9B and 9C show flare ends 2, 4 of clip 10 essentially midway in keyway 70. In other words, in the fully compressed operational mode shown in FIG. 9A, flare ends 2, 4 and the other portions of the terminal ends of clip 10 are closer to floor elements 88, 89 as compared with roof elements 80, 81. In contrast in FIG. 9B, clip flare elements 2, 4 are closer to the roof element 82 as compared to floor element 88 of keyway 70. This spacial situation is shown in detail in FIG. 9C. Clip flare element 2 is illustrated at a midway position in keyway 70, approximately midway between floor 88 of keyway 70 and roof element 80 of keyway 70. In this configuration, which is the post deposition clip release position, the clip jaws can be withdrawn proximally thereby removing or withdrawing the over hang of roof elements 84, 86 from flare elements 2, 4 of the clip. This movement is in an x axis direction or longitudinally.

Figure 9D:
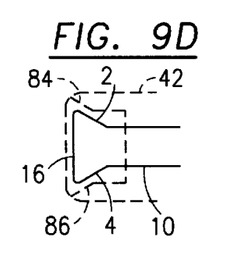
FIGS. 9D and 9E diagrammatically illustrate withdrawal of the clip applicator jaws (shown in broken lines) from the clip.
Figure 9E:
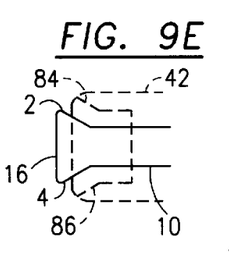

FIGS. 9D and 9E diagrammatically illustrate the movement of clip jaw 42, shown in broken lines, away from flare clip end 16. In FIG. 9D, clip jaw 42 has not been moved proximally away from flare clip end 16. In FIG. 9E, sidewalls 84, 86 of clip 42 are moved away from flare elements 2, 4 of clip end 16. The resulting freedom of the clip jaws enables the operator to further open the clip jaws 42, 44 as necessary. To extract the jaws, the jaws must be in the partially closed instrument insertion position shown in FIG. 7B.

Figure 10A:
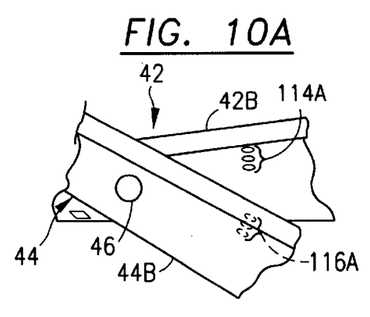
FIGS. 10A–10C diagrammatically illustrate tactile response indicators for the partially closed, instrument insertion position and the fully closed clip compressed position and the post deposition clip release position (excepting FIG. 10C which shows a two position tactile response indicator)
Figure 10B:
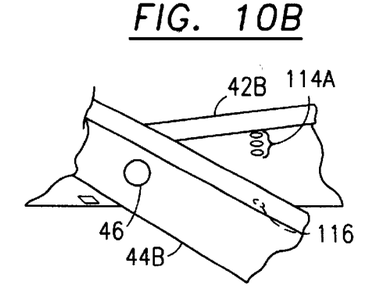
Figure 10C:
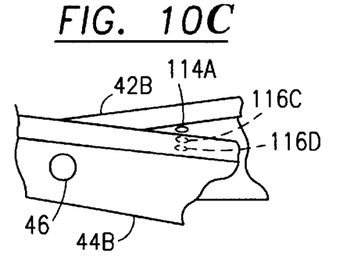

FIGS. 10A–10C diagrammatically show tactile response indicators for the fully opened position (FIG. 10A), and partially closed insertion position (FIG. 10C). In FIG. 10A, three tactile response units 114A are formed on proximal section 42B of clip jaw 42. A complementary group of tactile response units 116A are formed on proximal segment 44B of clip jaw 44. In FIG. 10B, three tactile response units 114A are formed on proximal segment 42B and only a single tactile response unit 116 is formed on proximal segment 44B of the other clip jaw. These tactile response units may take any complementary form, such as bumps, ribs or corresponding recesses in the opposite surface such that the user is tactily informed when the system reaches the partially closed instrument insertion position (FIG. 7B), the fully closed position (FIG. 7F), and the post deposition clip release position (FIG. 7G and FIGS. 9B and 8C). In FIG. 10C, a single tactile response unit 114A is utilized in connection with complemental tactile response units 116C, 116D. Two tactile response systems are utilized to show the partially closed instrument insertion position in the post deposition clip release position. The surgeon or the operator should be able to determine the fully closed position since that fully closed position would be beyond the "two click" position. As shown in the Closure Position Table (Mechanical Positions), the two clicks are represented by the partial close for insertion and the partial clip release position. From mechanical standpoint, the full closure for clip deposition is beyond the partial close for insertion and the partial clip release position. Hence, two tactile response indicators may be provided since the surgeon can easily determine that an additional compressive force is required to fully compress the clip on blood vessel 120 which is beyond the "two click" position. Alternatively, response point 116D may operate as a detent which temporarily stops further clip jaw open movement after complete clip compression. During clip compression (FIG. 7F), the clip jaws may recoil open. Response point 116D may operate as a detent to temporarily latch the jaws at the post deposition position.

Figures 11A, 11B:
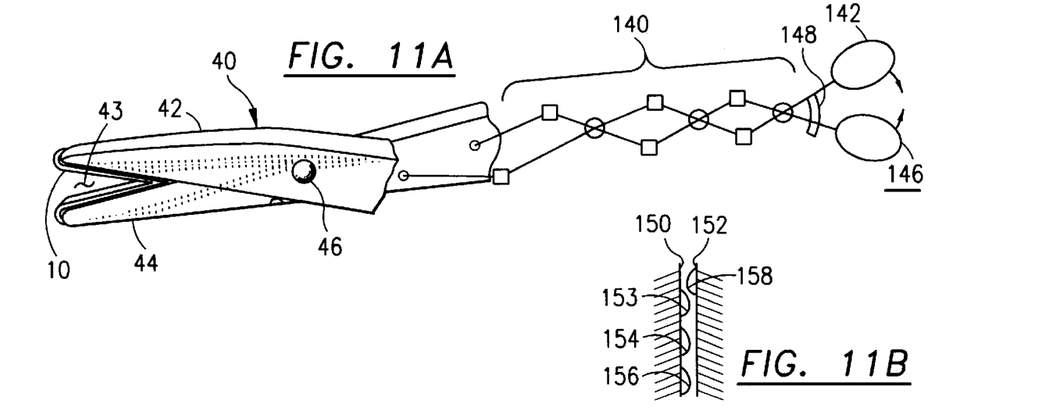
FIG. 11A diagrammatically shows a closure system indicative of a plurality of links and pivots having a handle on a proximal end of the instrument and the clip applier jaws at a distal end of the instrument.
FIG. 11B diagrammatically illustrates tactile response indicators on the handle grip of FIG. 11A.

FIG. 11A diagrammatically shows the surgical instrument which closes clip jaws 42, 44 like a scissor about common axis 46. A link and pivot mechanical system to transmit the compressive force longitudinally from the handle is diagrammatically illustrated along elongated segment 140. Other mechanical transmission systems may be utilized. At the proximal end of the instrument, handles 142, 146 are provided. By compressing handles 142, 146 together as shown by the arrow indicators in FIG. 11A, the mechanical linkage system 140 causes clip jaws 42, 44 to rotate about common axis 46 thereby closing jaws 42, 44 and the captured clip 10.

FIG. 11B shows a tactile response system which may be configured on spanning member 148 intermediate handles 142, 146. Spanning member 148 consists of surface 150 and surface 152. Surface 150 includes tactile response units 153, 154 and 156. Surface 152 includes tactile response unit 158. When tactile response unit 158 moves over response surfaces 153, 154 and 156, the user is provided with a tactile response indicator which is indicative of the open or close position of clip jaws 42, 44. These closure positions represent the closure positions of the clip jaws 42, 44 discussed above.

The present invention may be utilized in conjunction with surgical clips having certain gripping surfaces on the inboard side. Other surgical clip gripping surfaces may be utilized. The grip surfaces shown in FIGS. 12A–12E provide an example.

Figures 12A, 12B, 12E:
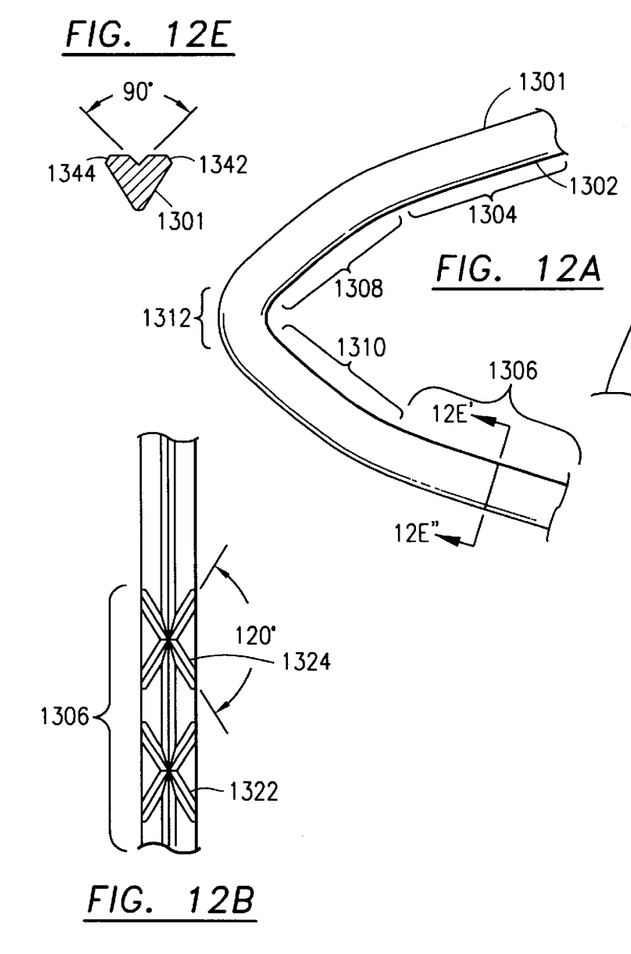
FIG. 12A diagrammatically illustrates a side view of a surgical clip.
FIG. 12B diagrammatically illustrates the surgical clip with two X-shaped channels on the terminal planar facial segment.
FIG. 12E diagrammatically illustrates a cross-section of the clip from the perspective of section line 12E'–12E" in FIG. 12A.

FIGS. 12A–12E diagrammatically illustrate the surgical clips. As shown in FIG. 12A, surgical clip 1301 is generally U-shaped. The clips have a clip face 1302 and near terminal facial segments 1304, 1306. Clip 1301 has intermediate facial segments 1308, 1310. Clip 1301 is bent in region 1312. Facial segments 1304, 1306, 1308 and 1310 are generally planar, that is, the clip portions that interface with the blood vessel are primarily planar except for the triangular or V-shaped channels cut or formed therein. Near terminal planar facial segment 1306 is shown in FIG. 12B. The clip face 1302 includes a longitudinal center channel 1320 which has a triangular or V-shaped cross-section. The triangular cross-section of center channel 1320 is shown in FIG. 12E. FIG. 12E is a cross-sectional view of clip 1301 from the perspective of section line 12E'–12E" in FIG. 12A. The longitudinal center channel 1320 extends through all of the planar facial segments 1304, 1306, 1308 and 1310.

Figure 12D:
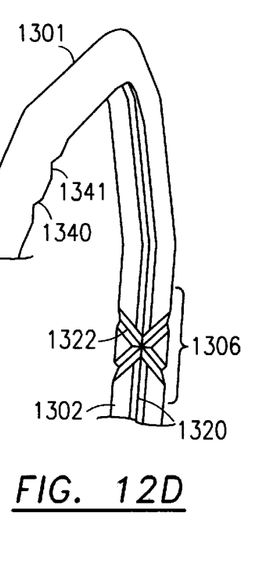
FIG. 12D diagrammatically illustrates a perspective view of the surgical clip showing the X-shaped channel on the terminal, planar facial segment and the longitudinal center channel.

In FIG. 12D, terminal planar facial segment 1306 includes an X-shaped channel 1322. The vertices of this X-shaped channel 1322 are coextensive with the longitudinal center channel 1320.

In FIG. 12B, terminal planar facial segment 1306 includes a first and a second X-shaped channel 1322, 1324. The legs of the X-shaped channel are angularly disposed at approximately 120°. The X-shaped channels have a triangular cross-sectional shape as shown at channel end segments 1340, 1341 on clip 1301 shown in FIG. 12E.

Clip 1301 includes a chamfer 1342, 1344 at its outer, opposing, lateral edges.

In a preferred embodiment, the clips are constructed in three sizes, small, medium and large. The legs of the clip are not parallel but are abducted to fit a clip holder. The X-shaped channels on the terminal planar facial segments and the longitudinal center channel provide a tire grip providing high traction for the clip on the blood vessel or organic structure. The lines of this X-shaped pattern with its coextensive vertices along the longitudinal center channel provide depressions in bas relief on the active clip faces which increase the frictional grip of the clip on the blood vessel from all angles.

The clips are constructed of titanium or tantalum. The clips are also designed with a greater angle to the diverging leg segments defining terminal planar facial segments 1304, 1306, in order to fit the clip jaws. Alternatively, the cross-sectional aspect of clip 1301 (shown as a triangle in FIG. 12E) may be rectilinear. The flared ends or hook ends are not shown in FIGS. 12A–12E.

Surgical instrument 10 may also utilize a handle providing additional tactile responses. One such handle is shown in FIGS. 13A and 13B.

Figure 13A:
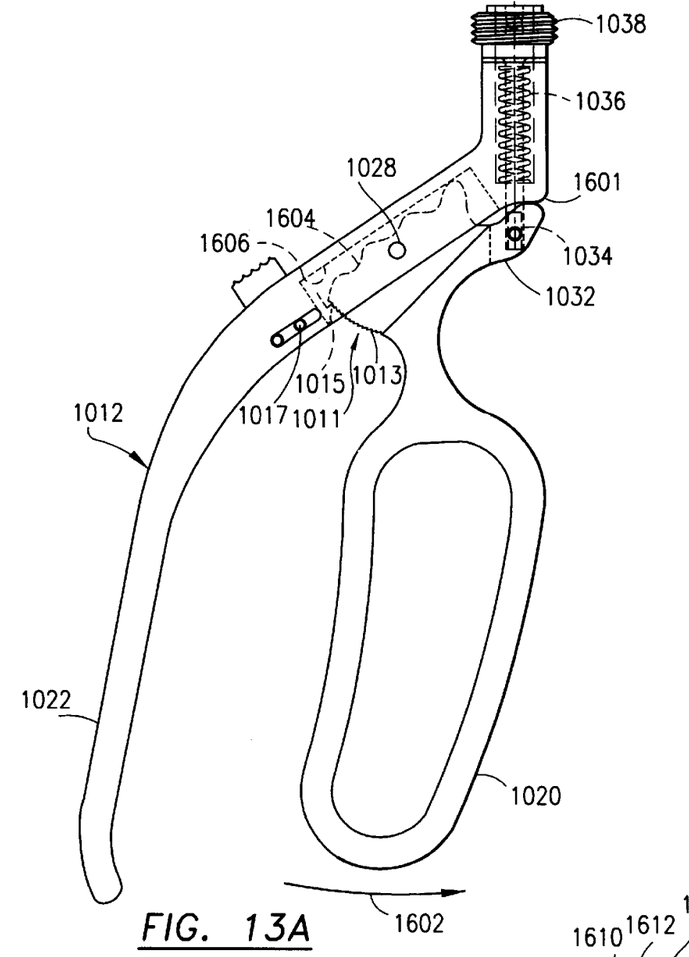
FIG. 13A diagrammatically illustrates one embodiment of a handle for the surgical instrument and one type of tactile response surface.

FIG. 13A diagrammatically illustrates handle 1012. Handle 1012 includes stationary grip member 1022 and movable handle member 1020. Movable member 1020 is pivotally mounted to stationary member 1022 via pivot pin or bolt 1028. Stem 1032 of movable member 1020 is movably coupled to an actuator rod 1034. Stem 1032 is biased toward handle stop 1601 due. to biasing spring 1036. Of course, other biasing mechanisms could be utilized such as leaf spring and pneumatic or hydraulic springs or mechanisms. In this manner, movable handle member 1020 is biased in the "full open" direction shown by arrow 1602.

Movable handle 1020 includes a tactile response surface 1604. In the illustrated embodiment, tactile response surface 1604 is an undulated or wavy surface. Other types of tactile response surfaces could be utilized. Handle 1012 includes a racket system 1011 which includes fine tooth gear 1013, swing lock bar 1015 and control button 1017. The racket locks the handle in a compressed mode and the operator releases the lock by moving control bar rearward. Tactile surface 1604 could be a plurality of nubs or protrusions which ride on and bump against tactile response wall 1606 of stationary handle member 1022.

Figure 13B:
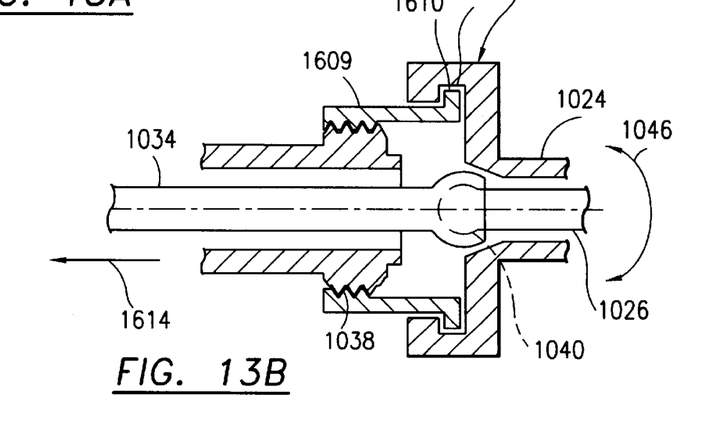
FIG. 13B diagrammatically illustrates the coupling between a handle actuator member and the longitudinally movable rod, and particularly shows the ability of the operator to rotate the elongated tube thereby rotating the attached end piece.

FIG. 13B diagrammatically illustrates details of the coupler section between handle 1012 and the elongated tube 1024 as well as the longitudinally movable rod 1026. Inboard handle segment has a male threaded joint 1038 which threads onto a female threaded section 1609. Female threaded section, at its inboard side, includes a rotatable coupling illustrated, in this embodiment, as a radially protruding ridge 1610. Outer rotating coupling 1042 forms a channel 1612 within which is captured radially extending ridge 1610. In this manner, the user can rotate female rotating unit 1042 relative to male rotating coupler 1610 as shown by the double headed arrow 1046. This rotation in direction 1046 rotates the elongated tube 1024 and therefore rotates the clip jaws.

Actuator rod 1034, in this illustrated embodiment, includes a ball and socket joint within which ball 1040 of movable rod 1026 is placed. In this manner, when actuator 1034 is retracted as shown by arrow 1614, rod 1026 is also retracted. The dimensions and the sizing of various components in FIG. 13B do not reflect actual size or dimensional relationships of the components. For example, movable rod 1026 may be closely captured by tube 1024. In this manner, rod 1026 may have various types of cross-sectional configurations. However, the ability of the operator to move the clip jaws by rotating female coupler 1042 may be affected by the cross-sectional configuration of rod 1026.

In operation, when the operator compresses handle 1020 toward stationary handle 1022 (a direction opposite arrow 1602), the user feels tactile response surface 1604 as it bumps against response wall 1606. Response wall 1606 is defined in the stationary handle member 1022. This informs the operator via tactile sensation that rod 1026 has retracted to a certain linear position which may be compressed to a first close position.

Figure 14:
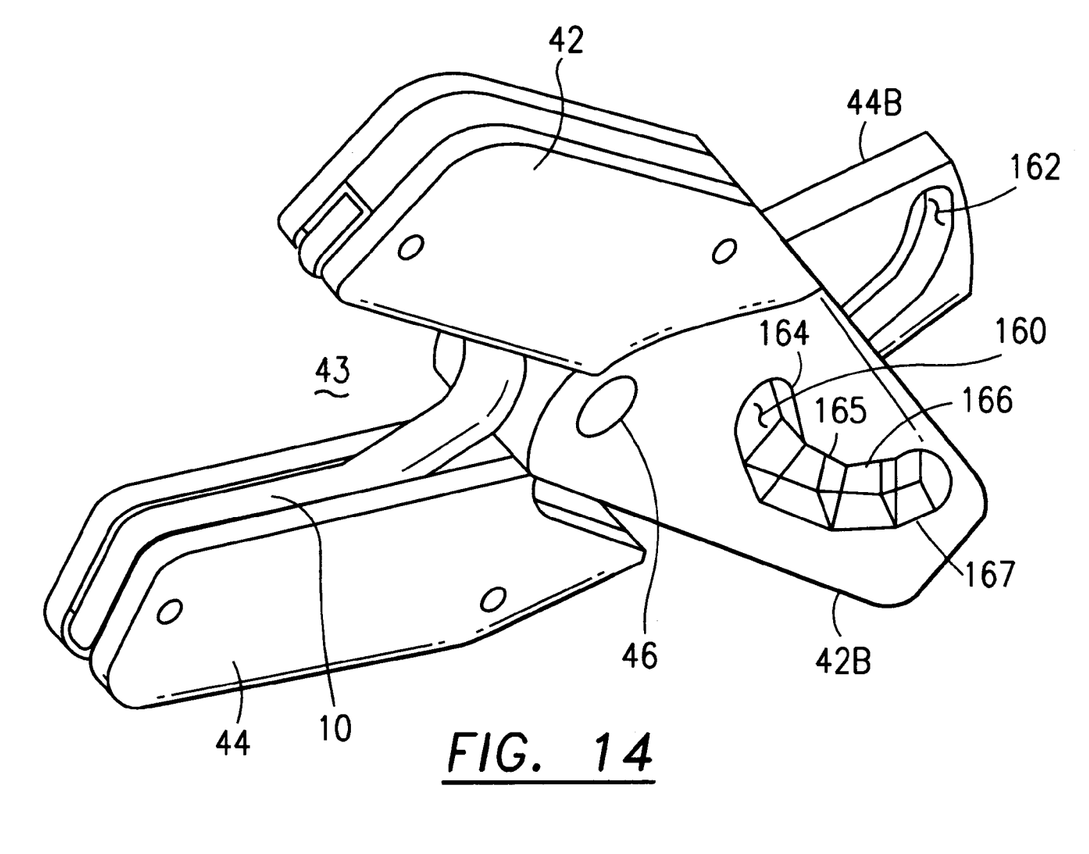
FIGS. 14 and 15 diagrammatically illustrate a clip applier closure system utilizing a cam longitudinally moving in a cam follower channel.
Figure 15:
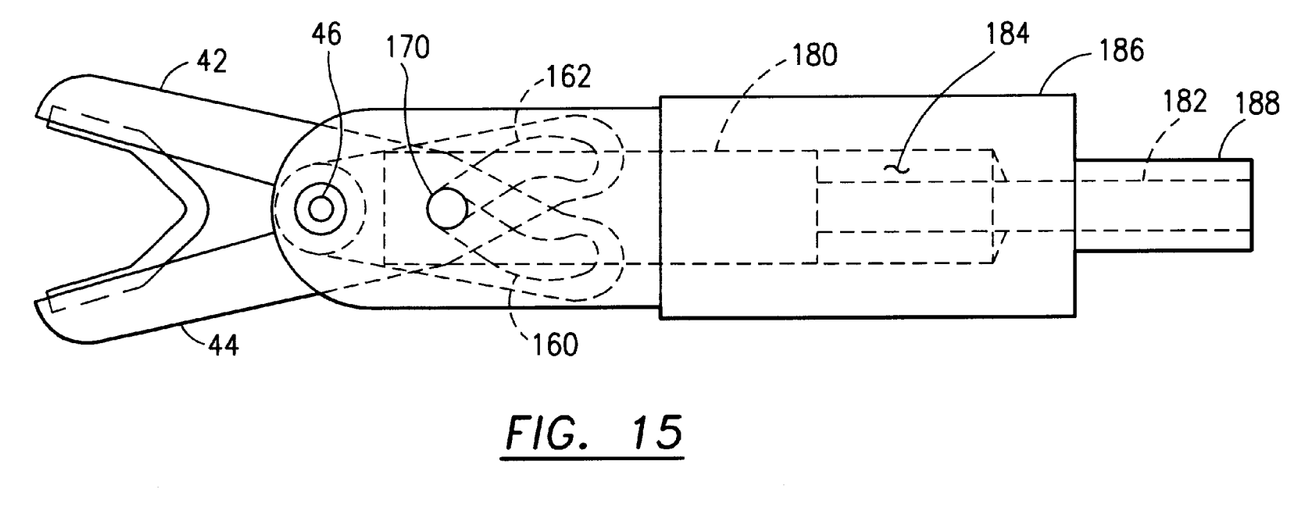

FIGS. 14 and 15 diagrammatically illustrate one embodiment to convert longitudinal movement into pivotal or rotational movement about jaw axis 46. In FIGS. 14 and 15, clip jaws 42, 44 have proximal segments 42B and 44B which respectively define cam following channels 160, 162. Clip 10 is retained in clip jaw mouth 43 by an appropriate channel system as described above. Clip jaws 42, 44 rotate about common axis 46. This rotation or pivotal movement is accomplished by a cam moving through cam follower channels 160, 162. In the illustrated embodiment, cam follower channels 160, 162 are segmented into regions 164, 165, 166 and 167 representing different speeds and degrees of compression. In other words, clip jaws 42, 44 close at a certain rate when the cam moves through initial cam follower channel 164, at a different rate when the cam moves through cam follower channel 165, at a further different rate when the cam moves through cam follower 166 and a different rate when the cam follower moves through cam follower channel 167.

FIG. 15 shows cam 170 which moves through cam follower channel 162 and cam follower channel 160. Cam 170 is attached to a slender bar 180 which, in turn, is attached to a longitudinal actuator 182. Actuator 182 may be connected to actuator rod 1026 in FIG. 13B. Bar 180 moves within slot 184. Bar 180 and cam 170 and actuator 180 move longitudinally with respect to stationary member 186 and elongated, stationary tube 188. Common axis 46 is mounted in a stationary position by attachment to stationary member 186 and stationary tube 188. The handle, discussed above and other handles known to persons of ordinary skill in the art, can provide longitudinal movement of longitudinal actuator rod 182 relative to stationary member 186. When cam 170 connected to movable rod 182 moves longitudinally and cam follower channels 160, 162, clip jaws 42, 44 open and close.

In another embodiment, cam follower channels 160, 162 are linear. In this embodiment, the closure rate of clip jaws 42, 44 based upon longitudinal movement of cam 170 in the clip follower channels is uniform. Channels 160, 162 do not bend and are exclusively linear. Cam 170 is typically a laterally positioned rod or pin for both embodiments.

Figure 16A:
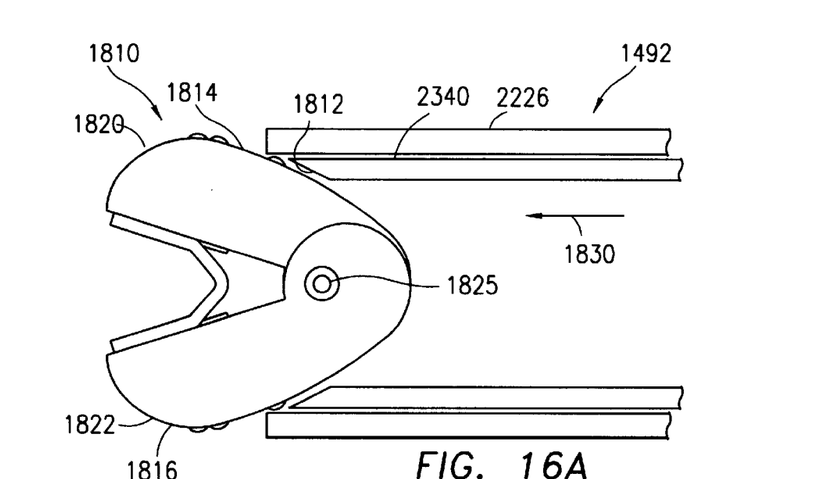
FIGS. 16A through 16C diagrammatically illustrate exterior cam surfaces on clip jaws which are closeably actuated by the longitudinal extension of a rod, tube or extending actuation member.
Figure 16B:
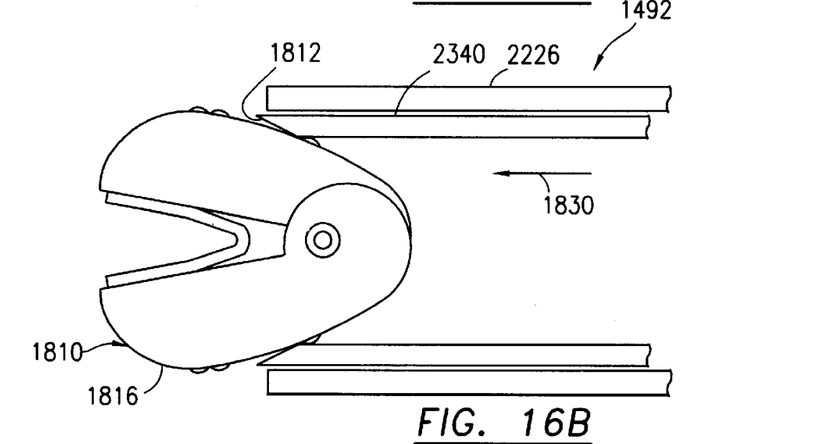
Figure 16C:
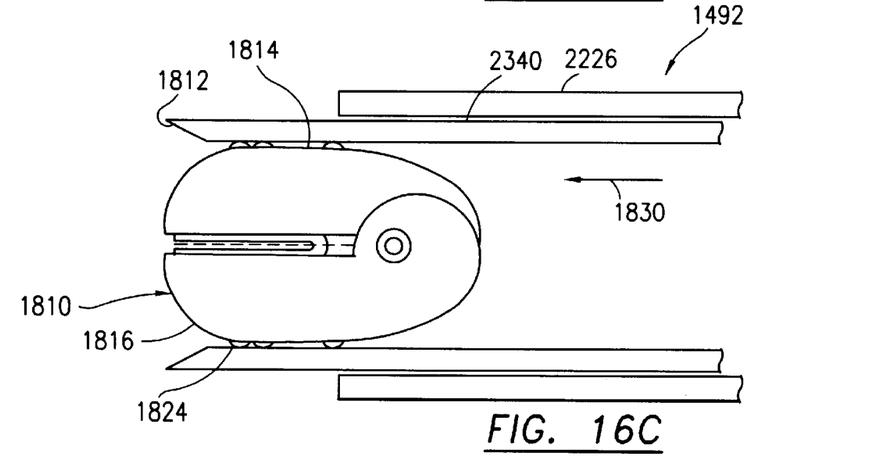

FIGS. 16A–16C diagrammatically illustrate side views of appliance clip jaws with cam follower surfaces. FIG. 16A diagrammatically illustrates appliance jaws 1810 in a fully opened position; FIG. 16B diagrammatically illustrates appliance jaws 1810 partially closed; and FIG. 16C diagrammatically illustrates the appliance jaws in a substantially closed position. The primary difference between cam actuated clip jaws 1810 and the clip jaws shown in FIGS. 14 and 15 is the utilization of clip action cam follower surfaces rather than clip action cam follower channels. In FIGS. 16A–16C, surgical appliance 1492 includes a stationary tube or elongated member 2226 and a longitudinally movable cam actuator member 2340. Cam actuator member 2340 includes a forwardly disposed cam surface 1812 which operates on cam follower surfaces 1814 and 1816 on the jaws. The lower jaw member has a cam follower surface 1816. Surfaces 1814, 1816 may be complementary shaped such that the jaw members 1820, 1822 close substantially simultaneously. Jaw members 1820, 1822 are pivotally disposed about common lateral axis 1825. Common lateral axis 1825 is maintained in a stationary position with respect to elongated tube 2226 of surgical appliance 1492. Cam actuator 2340 may have side slots for pivot pin 1825 mounted on stationary tube 2226.

As cam actuator member 2340 moves longitudinally outboard or forward, extending as shown by arrow 1830, initially jaw members 1820, 1822 close. This is shown diagrammatically in FIG. 16A. Cam surface 1814 includes a lateral extension or hump at that particular longitudinal position of movable rod or cam actuator member 2340. This provides a tactile response to the operator. The longitudinal position of actuator 2340 is noted with respect to stationary rod or tube 2226. Essentially, cam actuator member forward surface 1812 has not engaged the outboard extending surface of the tactile response bump at that longitudinal extension position.

In FIG. 16C, cam actuator member surface 1812 has moved beyond the closure point after acting upon lateral extensions or humps on the cam follower surface 1814, 1816. It should be noted that multiple closure rates and times (based upon longitudinal extension positions) may be programmed or cut into or formed by the cam follower surfaces 1816, 1814.

Other clip jaw closure systems may be utilized.

The claims appended hereto are meant to cover modifications and changes within the scope and spirit of the present invention.

What is claimed is:

1. A surgical clip comprising a substantially U or a V shape body defined by clip legs extending from an apex and respective flared terminal ends on corresponding clip legs, said clip legs lying in a clip defined plane having a clip lateral span and each said flared terminal end having an end lateral span slightly extending outboard from said clip lateral span, each respective said clip leg includes a inboard surface with a longitudinal center channel and at least one X-shaped channel, a vertex of said X-shaped channel being coextensive with said longitudinal center channel.

2. A surgical clip as claimed in claim 1 wherein each said terminal has a lateral end shape of one of a triangle, an oval, T-shape, an oblong, and wide end hexagonal shape.

3. A surgical clip as claimed in claim 1 including a plurality of X-shaped channels formed on said inboard clip leg surfaces.

4. A surgical clip comprising a substantially U or a V shaped body defining an apex and having two flared terminal ends opposite said apex, said body having a length and a lateral width, each said flared terminal end having a lateral flare width which is slightly larger than said body width, said body includes clip legs extending from said apex to said terminal ends, said clip legs having an inboard surface with a longitudinal center channel and at least one X-shaped channel, a vertex of said X-shaped channel being coextensive with said longitudinal center channel.

5. A surgical clip as claimed in claim 4 wherein each said terminal end has a lateral end shape of one of a triangle, an oval, T-shape, an oblong, and wide end hexagonal shape.

6. A surgical clip comprising a substantially U or a V shape body having an apex and two terminal ends opposite said apex, said body having a substantially uniform body lateral span and each said terminal end being flared and having an end lateral span slightly larger than said body lateral span, said body includes clip legs extending from said apex to said terminal ends, said clip legs having an inboard surface with a longitudinal center channel and at least one X-shaped channel, a vertex of said X-shaped channel being coextensive with said longitudinal center channel.

7. A surgical clip as claimed in claim 6 wherein each said terminal end has a lateral end shape of one of a triangle, an oval, a T-shape, an oblong, and wide end hexagonal shape.

8. A surgical clip comprising a substantially U or a V shaped body defined by clip legs extending from an apex and respective terminal ends on corresponding clip legs, each terminal end including a outboard hook, said clip legs, terminal ends and outboard hooks lying in a singular, clip defined plane wherein each respective said clip leg includes a inboard surface with said longitudinal center channel and at least one X-shaped channel, a vertex of said X-shaped channel being coextensive with said longitudinal center channel.

9. A surgical clip a claimed in claim 8 wherein said V-shape or U-shape clip body define, with said clip legs, a wide clip mouth, each said hook defines a hook mouth disposed on opposing side of said clip mouth and being open opposite said clip mouth.

10. A surgical clip as claimed in claim 9 wherein each said hook mouth is smaller than said clip mouth.

11. A surgical clip as claimed in claim 8 wherein a plurality of X-shaped channels are defined on one of said inboard surfaces.

12. A surgical clip as claimed in claim 11 including a plurality of X-shaped channels formed on said inboard clip leg surfaces.

13. A surgical clip comprising a substantially U or a V shaped body defined by clip legs extending from an apex and respective terminal ends on corresponding clip legs, said clip legs lying in a clip defined plane and each said terminal end having a lateral span extending outboard from said clip plane; wherein each said terminal end has a lateral end shape of one of a triangle, an oval, T-shape, an oblong, and wide end hexagonal shape and wherein each respective said clip leg includes a inboard surface with a longitudinal center channel and at least one X-shaped channel, a vertex of said X-shaped channel being coextensive with said longitudinal center channel.

\* \* \* \* \*